US008420846B2

(12) United States Patent
Dubey et al.

(10) Patent No.: US 8,420,846 B2
(45) Date of Patent: Apr. 16, 2013

(54) PROCESS FOR PRODUCING (S)-3-[(1-DIMETHYLAMINO)ETHYL] PHENYL-N-ETHYL-N-METHYL-CARBAMATE VIA NOVEL INTERMEDIATES

(75) Inventors: Shailendra Kumar Dubey, Uttar Pradesh (IN); Vikas Bansal, Uttar Pradesh (IN); Kamaljeet Pannu, Uttar Pradesh (IN); Sushil Kumar Dubey, Uttar Pradesh (IN)

(73) Assignee: Jubilant Life Sciences Limited, Noida (IN)

( * ) Notice: Subject to any disclaimer, the term of this patent is extended or adjusted under 35 U.S.C. 154(b) by 116 days.

(21) Appl. No.: 13/060,666

(22) PCT Filed: Aug. 25, 2009

(86) PCT No.: PCT/IB2009/006639
§ 371 (c)(1),
(2), (4) Date: May 15, 2011

(87) PCT Pub. No.: WO2010/023535
PCT Pub. Date: Mar. 4, 2010

(65) Prior Publication Data
US 2012/0022281 A1   Jan. 26, 2012

(30) Foreign Application Priority Data
Aug. 25, 2008 (IN) .......................... 2009/DEL/2008

(51) Int. Cl.
*C07C 303/28* (2006.01)
*C07C 309/73* (2006.01)
*C07C 271/42* (2006.01)
*C07C 269/00* (2006.01)

(52) U.S. Cl.
USPC ............................................. 558/48; 560/136

(58) Field of Classification Search .................... 558/48; 560/136
See application file for complete search history.

(56) References Cited

U.S. PATENT DOCUMENTS

| 4,948,807 A | 8/1990 | Rosin et al. |
| 5,602,176 A | 2/1997 | Enz |
| 7,683,205 B2 * | 3/2010 | Deshpande et al. .......... 560/136 |

FOREIGN PATENT DOCUMENTS

| EP | 1 939 172 | | 7/2008 |
| EP | 1939172 | * | 7/2008 |
| WO | 2004/037771 | | 5/2004 |
| WO | 2006/048720 | | 5/2006 |
| WO | 2008/037433 | | 4/2008 |

OTHER PUBLICATIONS

Wu et al, 2004, J. Med. Chem., vol. 47, p. 2887-2896.*

* cited by examiner

*Primary Examiner* — Wu-Cheng Winston Shen
*Assistant Examiner* — Karen Cheng
(74) *Attorney, Agent, or Firm* — Maschoff Brennan

(57) ABSTRACT

Disclosed herein are novel intermediates and process for large scale production of (S)-3-[(1-dimethylamino)ethyl] phenyl-N-ethyl-N-methyl-carbamate (rivastigmine) or its pharmaceutically acceptable salts employing the novel intermediates. Further provided are methods for producing the novel intermediates thereof.

20 Claims, No Drawings

PROCESS FOR PRODUCING (S)-3-[(1-DIMETHYLAMINO)ETHYL] PHENYL-N-ETHYL-N-METHYL-CARBAMATE VIA NOVEL INTERMEDIATES

FIELD OF THE INVENTION

This invention in general relates to a process for producing (S)-3-[(1-dimethylamino) ethyl]phenyl-N-ethyl-N-methyl-carbamate (rivastigmine) or pharmaceutically acceptable salts thereof. More particularly, the present invention provides novel intermediates, process for producing the same and employing the same for producing rivastigmine or pharmaceutically acceptable salts thereof.

BACKGROUND OF THE INVENTION (S)-3-[(1-Dimethylamino) ethyl]phenyl-N-ethyl-N-methyl-carbamate (rivastigmine) of Formula I or its pharmaceutically acceptable salts is known to possess cholinesterase inhibitor activity and is used in the treatment of Alzheimer's disease.

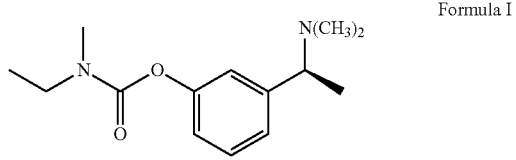 [SMILES: CCN(C)C(=O)Oc1cccc([C@H](C)N(C)C)c1]

Formula I

U.S. Pat. No. 4,948,807 discloses a method for the preparation of phenyl carbamate compounds by reacting α-m-hydroxyphenylisopropyldimethylamine or α-m-hydroxyphenylethyl dimethylamine with appropriate isocyanate or carbamoyl halides. The process using isocyanates involves the use of benzene as a solvent. Isocyanates such as lower alkyl isocyanates are hazardous to handle due to their toxic and non-volatile nature.

The other reported alternative is the use of carbamoyl halides along with reactive base like sodium hydride to prepare carbamate. However, the use of sodium hydride on commercial scale is hazardous and difficult to handle due to its pyrophoric and reactive nature.

U.S. Pat. No. 5,602,176 discloses resolution of the racemic rivastigmine by forming the diastereoisomeric salts with di-O,O'-p-toluoyl-D-tartaric acid and their separation by repeated crystallization. The (S)-enantiomer of rivastigmine is obtained by treating the salt with sodium hydroxide solution. Since the resolution is performed in the last step, about 50% of the racemic mixture (containing R-enantiomer) is wasted which results in low yield, thus making the process industrially less viable.

WO 2004037771 discloses the resolution of 3-[1-(dimethylamino)ethyl]phenol followed by reaction of its S-enantiomer with carbamoyl halide using strong base like sodium hydride. The main drawback of this process is the low yield (25-31%) obtained during the resolution of 3-[1-(dimethylamino)ethyl]phenol to get optically pure compound. Furthermore, the use of reactive base like sodium hydride on industrial scale is not only hazardous but also operationally difficult due to its pyrophoric and reactive nature.

WO 2006048720 discloses the resolution of 3-[1-(dimethylamino)ethyl]phenol using D-(+)-10-camphor sulphonic acid to obtain diastereomeric salt with a yield of only 25-30%.

EP 1939172 discloses another alternative method for producing rivastigmine comprising reacting (S)-3-[1-(methylamino)ethyl]phenol with carbamoyl halide to form an intermediate, which is subjected to reductive amination reaction or methylation reaction by reacting with methyl halide to obtain rivastigmine. The (S)-3-[1-(methylamino)ethyl]phenol is obtained by the resolution of racemic 3-[1-(methylamino)ethyl]phenol or dealkylation of (S)-1-(3-methoxyphenyl)ethylmethylamine. The diastereomeric salts of racemic 1-(3-methoxyphenyl)ethylmethylamine are formed by reacting with D-(−)-tartaric acid and finally releasing the S-enantiomer by treating with sodium hydroxide solution. This process requires additional crystallizations steps to obtain tartrate salt with a yield of 27% only. Further, the process employs carcinogenic and toxic methyl iodide. Titanium isopropoxide, sodium hydride, hydrobromic acid and sodium cyanoborohydride used in various stages of synthesis as disclosed in various examples are expensive and make the process highly economically unfavorable. Moreover, carbamate formation involves the use of sodium hydride that requires special handling during work-up.

The processes disclosed in the prior art involves use of hazardous chemicals like isocyanate, low yield in the resolution step and use of expensive chemicals like titanium isopropoxide, sodium hydride, hydrobromic acid and sodium cyanoborohydride, thereby making the process unsuitable for commercial scale production.

Thus there exists a need for a safe, economically viable and efficient industrial process for producing rivastigmine and its pharmaceutically acceptable salt, which is free from above mentioned drawbacks. In addition the process provides high yield and high purity in environmentally friendly condition.

OBJECT AND SUMMARY OF THE INVENTION

It is an object of the present invention to provide an economically viable and environmental friendly process for producing (S)-3-[(1-Dimethylamino)ethyl]phenyl-N-ethyl-N-methyl-carbamate (rivastigmine) or its pharmaceutically acceptable salts.

It is another object of the present invention to provide high yielding and industrially feasible process for producing rivastigmine or its pharmaceutically acceptable salts, wherein the process provides high yield of the desired product.

It is one other object of the present invention to provide a process for producing rivastigmine or its pharmaceutically acceptable salts, wherein the process avoids the use of hazardous chemicals and is operationally simple.

It is yet another object of the present invention to provide an improved process for producing rivastigmine or its pharmaceutically acceptable salts, wherein the process provides highly chiral pure compounds without multiple purification steps in an environmental friendly reaction condition.

The above and other objects are further attained and supported by the following embodiments described herein. However the scope of the invention is not restricted to described embodiments herein after.

In accordance with an embodiment of the present invention, there is provided a process for producing (S)-3-[(1-dimethylamino)ethyl]phenyl-N-ethyl-N-methyl-carbamate (rivastigmine) or its pharmaceutically acceptable salts via novel intermediates comprises of reacting a compound of Formula III with a protecting agent of Formula RX in presence of a base and solvent to obtain compound of Formula IV, optically resolving the compound of Formula IV employing a resolving agent of compound HA to obtain a compound of Formula V, followed by converting the diastereomeric compound of Formula V in presence of a base and a solvent to obtain a compound of Formula VI, methylating the compound of Formula VI using a formylating agent in presence of an organic solvent to obtain a compound of Formula VII, followed by deprotecting the compound of the Formula VII in presence of an acid or base to obtain a compound of Formula VIII and reacting compound of Formula VIII with carbamoyl halide in presence of a base in a solvent to obtain rivastigmine. The resultant rivastigmine is further treated with an optically active acid to obtain a corresponding salt thereof.

In accordance with another embodiment of the present invention, R group is a substituted sulphonyl group selected from phenyl sulphonyl, $C_{1-4}$alkyl substituted phenyl sulphonyl, $C_{1-4}$ alkoxy substituted phenyl sulphonyl, benzoyl sulphonyl or substituted benzoyl sulphonyl or any phenol protecting group.

In accordance with still another embodiment of the present invention, there is provided a novel intermediate compound of Formula IV for producing the rivastigmine or pharmaceutically acceptable salt thereof and a process for producing the same.

In accordance with yet another embodiment of the present invention, there is provided a novel intermediate compound of Formula V for producing the rivastigmine or pharmaceutically acceptable salt thereof and a process for producing the same.

In accordance with a still another embodiment of the present invention, there is provided a novel intermediate compound of Formula VI for producing the rivastigmine or pharmaceutically acceptable salt thereof and a process for producing the same.

In accordance with still another embodiment of the present invention, there is provided a novel intermediate compound of Formula VII for producing the rivastigmine or pharmaceutically acceptable salt thereof and a process for producing the same.

In accordance with yet another embodiment of the present invention, there is provided a process for producing a compound of Formula VIII for producing rivastigmine of Formula I or pharmaceutically acceptable salt thereof from a novel intermediate of the Formula VII.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention provides a commercially viable and industrially feasible process for producing (S)-3-[(1-Dimethylamino)ethyl]phenyl-N-ethyl-N-methyl-carbamate (rivastigmine) of Formula I or its pharmaceutically acceptable salts. The process employs novel intermediates of the present invention for producing the rivastigmine thereof.

The present invention in addition provides a high yielding process for producing the rivastigmine or its pharmaceutically acceptable salts of high purity employing minimum steps. Moreover, the present invention employs non-hazardous and less expensive raw materials.

Further, the present invention discloses novel intermediates of Formula IV, V, VI and VII, for producing rivastigmine or its pharmaceutically acceptable salts and processes for producing thereof.

The process according to the present invention for producing (S)-3-[(1-dimethylamino)ethyl]phenyl-N-ethyl-N-methyl-carbamate (rivastigmine) of Formula I or its pharmaceutically acceptable salts via novel intermediates comprises of:

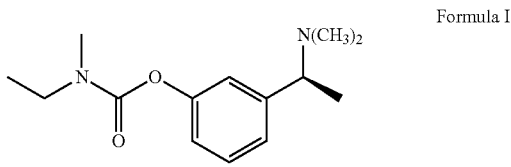 [SMILES: CCN(C)C(=O)Oc1cccc([C@H](C)N(C)C)c1]

Formula I a) reacting a compound of Formula III with a protecting agent of Formula RX in presence of a base and solvent to obtain compound of Formula IV,

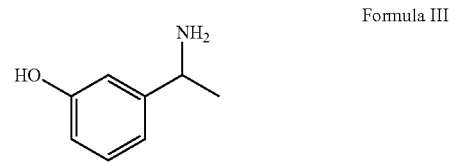

Formula III

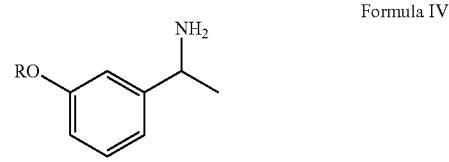

Formula IV wherein R is a substituted sulphonyl group and X is a halogen;

b) optically resolving the compound of Formula IV employing a resolving agent of compound HA to obtain a compound of Formula V;

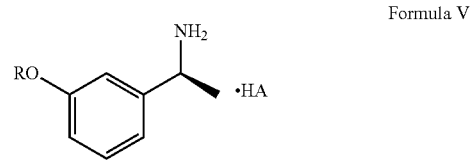

Formula V wherein HA is a optically active acid c) converting the diastereomeric compound of Formula V in presence of a base and a solvent to obtain a compound of Formula VI;

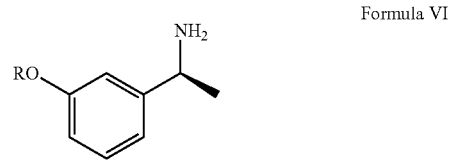

Formula VI d) methylating compound of the Formula VI using a formylating agent in presence of an organic solvent to obtain a compound of Formula VII;

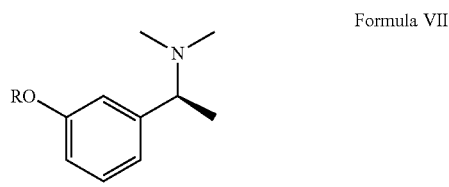

Formula VII e) deprotecting compound of the Formula VII in presence of an acid or base to obtain a compound of Formula VIII;

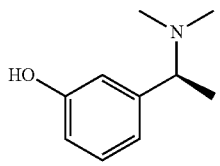

Formula VIII f) reacting compound of Formula VIII with carbamoyl halide in presence of a base in a solvent to obtain rivastigmine of Formula I and further treating the resultant rivastigmine with optically active acid to obtain a salt thereof.

According to the present invention, the starting compound of Formula III is prepared from 3-hydroxyacetophenone by the methods known in the prior arts.

According to the present invention, the substituted sulphonyl group R is selected from phenyl sulphonyl, C1-4alkyl substituted phenyl sulphonyl, C1-4 alkoxy substituted phenyl sulphonyl, benzoyl sulphonyl or substituted benzoyl sulphonyl or any phenol protecting group.

According to the present invention, hydroxy group of the compound of Formula III is treated with the protecting agent of Formula RX in presence of a base and solvent to obtain a novel intermediate of Formula IV.

The base used herein is selected from an organic or inorganic base. Preferably the organic base is selected from N,N-dimethylamine, N-ethyl-N-methyl amine, triethylamine, N,N-dimethylbenzylamine, N,N-diethylbenzylamine, N-methyl morpholine, dimethylaminopyridine, pyridine and the like. The inorganic base is selected from alkali or alkaline earth metals hydroxides, carbonate, hydrides, wherein the alkali and alkaline earth metal is selected from lithium, sodium, potassium, calcium, magnesium and the like. The solvent used herein is selected from aromatic hydrocarbon, straight or branched chain alcohols, chlorinated solvents, ketones, esters, ethers or mixture thereof. In accordance with the present invention, the reaction is carried out at temperature from about −15 to 50° C. preferably at 0 to 35° C., more preferably between 25-30° C. for 1-4 h preferably 1-2 h.

According to the present invention, the resolution of the compound of Formula IV is carried out employing a resolving agent, which is a chiral (optically active) acid to obtain a novel intermediate of Formula V. The chiral acid employed in the process is selected from mandelic acid, tartaric acid, camphor sulphonic acid, dibenzoyl tartaric acid, diparatolyl tartaric acid and the like. Suitable solvent employed during the resolution is selected from water, lower alcohol, lower ketone, ethers, ester and mixture thereof. The reaction takes place at temperature between 20 to 80° C., preferably 45 to 50° C., most preferably between 25-30° C. for 1-4 h preferably 1-2 h.

According to the invention, a novel intermediate compound of Formula VI is set free by treating the diastereomeric salt of compound of Formula V in presence of base in a solvent. The base is selected from organic or inorganic. The inorganic base used according to the present invention is selected from alkali or alkaline earth metal hydroxide or carbonate such as sodium carbonate, potassium carbonate, magnesium carbonate, calcium carbonate, lithium carbonate or ammonia. The organic base is selected from N,N-dimethylamine, N-ethyl-N-methyl amine, triethylamine, diethylbenzylamine, N-methyl morpholine, or mixture thereof. The reaction takes place in presence of solvent selected from water, aromatic hydrocarbon, chlorinated hydrocarbon, esters, ether or mixture thereof. Preferred solvents are water, toluene, xylene, dichloromethane, chloroform and mixture thereof.

According to the present invention, methylation of the compound of Formula VI to a novel intermediate compound of Formula VII is performed using a formylating agent. The preferred formylating agent is selected from formic acid and formaldehyde solution or formaldehyde and sodium cyanoborohydride. Further, the methylation reaction optionally takes place in presence of organic solvent selected from aromatic hydrocarbon, chlorinated hydrocarbon, esters, ethers, alcohols, nitriles, amides and the like. Preferably the solvent is selected from toluene, dichloromethane, chloroform, ethyl acetate, acetone, acetonitrile, dimethylsulphoxide, dimethylformamide and the like. The reaction is carried out at a temperature between 40-80° C., preferably between 50-65° C. for 10-20 h preferably 14-16 h.

According to an embodiment of the present invention, the deprotection of novel intermediate compound of Formula VII to obtain the compound of the Formula VIII is carried out in presence of base in an organic solvent. The base is preferably inorganic selected from alkali or alkaline earth metal hydroxide, carbonates, hydrides, alkoxides and the like. The reaction can optionally take place in presence of acid selected from inorganic or mixture of organic and inorganic acid. Preferably the inorganic acid is selected from hydrochloric acid, nitric acid, sulfuric acid, trifluoroacetic acid and the like. The solvent used herein is selected from water, aromatic hydrocarbon, cyclic ethers, amides, alcohols, ketones, esters, polar aprotic solvents or mixture thereof. Preferably the solvent is selected from toluene, tetrahydrofuran, dimethylsulphoxide, dimethylformamide, dimethyl acetamide or mixture thereof. The reaction is carried out at a temperature between 20-35° C., preferably at room temperature for 1-6 hours preferably for 2-3 hours.

The compound of Formula VIII is optionally purified using solvent selected from cyclic hydrocarbon, esters, ethers, preferably, cyclohexane, ethyl acetate, methyl tertiary butyl ethers and the like.

In accordance with the invention, the resulting compound of the Formula VIII according to the present invention is subjected to carbamoylation reaction using carbamoyl halide, preferably N-ethyl-N-methylcarbamoyl chloride in the presence of base in suitable solvent to obtain the rivastigmine. Suitable base is selected from organic or inorganic base. Preferably the inorganic base is selected from alkali or alkaline earth metal hydroxide, carbonate and hydrides. Preferably the organic base is selected from triethylamine, N,N-dimethylamine, N-ethyl-N-methyl amine, N,N-dimethylbenzylamine, N,N-diethylbenzylamine, N-methyl morpholine or mixture thereof. The solvent used herein is selected from aromatic hydrocarbon, chlorinated hydrocarbon, esters, ethers, alcohols, ketones, nitriles, amides and the like. Preferred solvents are toluene, dichloromethane, ethyl acetate, acetone, acetonitrile, dimethylsulphoxide, dimethylformamide and the like. The reaction is carried out at temperature from about 40° C. to 80° C., preferably at 50 to 70° C., more preferably at 55-65° C. for 5-15 h preferably 8-10 h.

According to the present invention, rivastigmine of Formula I is optionally converted to desired pharmaceutically acceptable salt preferably tartarate salt by treating the rivastigmine of Formula I with an optically active tartaric acid. The rivastigmine hydrogen tartrate so obtained is optionally crystallized employing suitable solvent such as aliphatic alcohol, preferably methanol.

Example 1

Preparation of 1-(3-Hydroxyphenyl)ethylamine (III)

A mixture of 1000 ml of methanolic ammonia, 100 g of 3-hydroxyacetophenone, 25 g of molecular sieves and 10 g of Raney nickel was taken in an autoclave flask at 0-5° C. The autoclave flask was then closed and stirred for 6 h at 75-80° C. without applying hydrogen gas pressure. The reaction mass was further hydrogenated at 75-80° C. by applying 15-20 kg/cm$^2$ pressure of hydrogen gas and the reaction mixture was allowed to stir while maintaining the same conditions of temperature and pressure for 18-22 h. After the completion of the reaction, the reaction mixture was cooled to room temperature and filtered through hyflo bed. The hyflo bed was washed with 200 ml methanol and the solvent distilled off, under reduced pressure at a temperature of 60° C. The reaction mass was cooled to 0-5° C. and stirred for 1 h to obtain a slurry. The solid thus obtained was filtered, washed with ethyl acetate and dried to obtain the title compound.

Example 2

Preparation of 3-(1-Aminoethyl)phenyl)p-toluenesulfonate (IV)

A mixture of 600 ml of tert-butanol, 100 g of 1-(3-hydroxyphenyl)ethylamine (III) and 48 g of potassium hydroxide was heated at 80-85° C. for 1 h. The reaction mass was then cooled to room temperature and 100 ml of toluene was added. The reaction mixture was further cooled to 0-5° C. and p-toluenesulphonyl chloride solution (104.2 g dissolved in 300 ml toluene) was added to the mixture over 3-4 hours under stirring at 0-5° C. The temperature of the reaction mixture was allowed to rise to room temperature and stirred at same temperature for 2 hours. The progress of the reaction is monitored using HPLC/TLC. After the reaction completion, solvent was distilled off under reduced pressure at 50-55° C. and the reaction mass was cooled to room temperature. Water and toluene were added to the reaction mixture and stirred for 30-45 minutes. Subsequently the reaction mixture was filtered through hyflo bed. The layers were then separated and to the organic layer, 2% w/v sodium hydroxide solution (dissolved 4 g of sodium hydroxide in 200 ml of water) was added. The reaction mixture was allowed to stir for 30 minutes. After separating the aqueous layer, the organic layer was washed with water (4×200 ml) and concentrated under reduced pressure at 50-55° C. to obtain the title compound as oily mass.

Characterization data: I.R. (neat): 3480, 3448, 3091, 2908, 1495, 1453, 1307, 1247

$^1$HNMR (CDCl$_3$): 1.15-1.16 (3H, d), 2.34 (3H, s), 3.91-3.96 (1H, q), 6.74-6.76 (1H, m), 6.82 (1H, broad signal), 7.12-7.14 (2H, m), 7.20-7.22 (2H, d; J=7.2 Hz), 7.58-7.60 (2H, d; J=8.4 Hz).

$^{13}$C-NMR (CH$_3$OD): 21.67, 25.51, 50.72, 119.77, 120.60, 124.51, 128.52, 129.57, 129.71, 132.29, 145.39, 149.71, 149.88.

ES (m/z): 291 (M+1).

Example 3

Preparation of (S)-3-(1-Aminoethyl)phenyl)p-toluenesulfonate mandelate (V)

77.64 g of (S)-(+)-mandelic acid and 3-(1-aminoethyl)phenyl)p-toluenesulfonate (IV) (from Example 2) was stirred in a mixture of acetone (400 ml) and water (70 ml) at 55-60° C. for 30 minutes to obtain a clear solution. The solution was then cooled to room temperature and stirred for another 1 h and filtered. The solid thus obtained was washed with acetone and dried at 45-50° C. to obtain crude compound. The resulting solid was taken in 750 ml of water and heated to 80-85° C. for 30 minutes. The reaction mass was then cooled at room temperature and stirred for 5-6 h. The solid thus obtained was filtered and washed with water and dried at 45-50° C. to obtain the title compound.

Characterization data: I.R. (KBr, cm-1): 3435, 3094, 2926, 1574, 1538, 1372, 1176

$^1$HNMR (CH$_3$OD): 1.44-1.46 (3H, d), 2.43 (3H, s), 4.29-4.34 (1H, q), 4.85 (1H, s), 6.95-6.98 (1H, m), 7.15 (1H, broad signal), 7.19-7.23 (1H, m), 7.25-7.29 (2H, t), 7.33-7.36 (2H, m), 7.39-7.41 (2H, d, J=8 Hz), 7.43-7.45 (2H, d, J=7.2 Hz), 7.68-7.70 (2H, d, J=8.4 Hz).

$^{13}$C-NMR (CH$_3$OD): 20.92, 21.69, 51.55, 76.17, 122.06, 123.82, 126.70, 127.98, 128.35, 129.12, 129.71, 131.17, 131.69, 133.46, 142.38, 143.46, 147.46, 151.44, 179.45.

ES (m/z): 292 (M+1).

Example 4

Preparation of (S)-3-(1-Aminoethyl)phenyl)p-toluenesulfonate (VI)

100 g of (S)-3-(1-Aminoethyl)phenyl)p-toluenesulfonate mandelate (V), 220 ml of water and 550 ml of toluene were taken into a round bottom flask. The pH of reaction mixture was adjusted to 10-11 using liquid ammonia (~50 ml). The resulting mixture was stirred for another 30 minutes to obtain a clear solution. After separating the organic layer, the aqueous layer was washed with toluene. The combined toluene layer was washed with water and concentrated under reduced pressure at 50-55° C. to obtain the title compound.

Characterization data: I.R. (neat): 3480, 3448, 3091, 2908, 1495, 1453, 1307, 1247

$^1$HNMR (CDCl$_3$): 1.15-1.16 (3H, d), 2.34 (3H, s), 3.91-3.96 (1H, q), 6.74-6.76 (1H, m), 6.82 (1H, broad signal), 7.12-7.14 (2H, m), 7.20-7.22 (2H, d, J=7.2 Hz), 7.58-7.60 (2H, d; J=8.4 Hz).

$^{13}$C-NMR (CH$_3$OD): 21.67, 25.51, 50.72, 119.77; 120.60, 124.51, 128.52, 129.57, 129.71, 132.29, 145.39, 149.71, 149.88.

ES (m/z): 291 (M+1).

Chiral purity: 99.54%, HPLC purity: 100%, $[\alpha]_D^{25}$ –14.28° (C=1, MeOH)

Example 5

Preparation of (S)-[3-(1-Dimethylamino)ethyl]phenyl)p-toluenesulfonate (VII)

(S)-3-(1-Aminoethyl)phenyl)p-toluenesulfonate (VI) obtained in Example 4 was taken in 385 ml of water and cooled to 10-15° C. Formic acid (33.3 ml in 33 ml water) was added slowly to the reaction mixture over a period of 30 minutes under stirring followed by addition of formaldehyde solution (55.4 ml) over 30 minutes. The reaction mixture was then heated to 60-65° C. for 14-16 hours and monitored by HPLC/TLC. After the reaction completion, the reaction mass was cooled to room temperature and the pH of the resulting mixture was adjusted to 1-2 with concentrated hydrochloric acid. Subsequently, 330 ml of toluene was added and stirred for 30 minutes. After separating the organic layer, the aqueous layer was washed with toluene (2×220 ml). To the aqueous layer, toluene (330 ml) was added and the pH of the mixture adjusted to 9-10 with liquid ammonia. The reaction mixture was then stirred for 30 minutes. The layers were separated and aqueous layer washed with toluene. The combined organic layer was concentrated under pressure to yield the title compound as oily mass, which is further, used in the next step without purification.

Characterization data: I.R. (Neat): 2819, 2771, 3067, 2978, 1599, 1583, 1374, 1179

$^1$HNMR (CH$_3$OD): 1.17-1.18 (3H, d), 2.00 (6H, s), 2.33 (3H, s), 3.16-3.18 (1H, q, J=6.8 Hz), 6.81-6.82 (1H, t), 6.93-6.96 (1H, m), 7.14-7.15 (1H, m), 7.20-7.24 (1H, t), 7.27-7.29 (2H, d, J=8 Hz), 7.61-7.64 (2H, d, J=8.4 Hz).

$^{13}$C-NMR (CH$_3$OD: 20.07, 21.66, 43.01, 66.03, 122.15, 122.48, 127.53, 129.48, 130.51, 130.84, 138.60, 146.02, 146.80, 150.76.

ES (m/z): 320 (M+1).

Example 6

Preparation of (S)-[1-(3-Hydroxyphenyl)ethyl]dimethylamine (VIII)

44.6 g of KOH pellets was taken in 300 ml of methanol at room temperature under nitrogen atmosphere. The suspended solution was then cooled to 10-15° C. To the resulting solution, methanolic solution of (S)-[3-(1-Dimethylamino)ethyl] phenyl)p-toluenesulfonate (VII) obtained in Example 5 was added over 30 minutes. The reaction mixture was stirred for 2-3 hours at room temperature. After completion of the reaction, the reaction mixture was filtered and washed with methanol. Methanol was removed completely under reduced pressure and water was added to the resulting reaction mixture. The reaction mixture was cooled to 10-15° C. and pH was adjusted between 1-2 using concentrated hydrochloric acid. Water was then added and the layers were mixed and separated. The aqueous layer was washed with toluene (3×200 ml). To the aqueous layer, ethyl acetate was added, followed by the adjustment of pH to 9.5-11 with liquid ammonia. After separating and washing the aqueous layer with ethyl acetate, the combined organic layer was concentrated under reduced pressure. Cyclohexane (100 ml) was then added and distilled off. Again 200 ml of cyclohexane was added to the residue and heated to 80-85° C. for 30 minutes. The reaction mass was cooled to room temperature and stirred for 1 hour. The solid thus obtained was washed with cyclohexane and dried to obtain the title compound.

Example 7

Preparation of (S)-(−)-Rivastigmine Tartrate

To a solution of 100 g of (S)-[1-(3-hydroxyphenyl)ethyl] dimethylamine (VIII) in 500 ml of acetone, pulverized potassium carbonate (125.2 g) was added. The reaction mixture was heated to 40-45° C. for 1 hour. A solution of N-ethyl-N-methylcarbamoyl chloride (77.5 g) in acetone (300 ml) was added to the reaction mixture and the temperature of the reaction mixture was raised to 55-60° C. followed by stirring at the same temperature for 8-10 hours. After the completion of the reaction, the reaction mixture was cooled and filtered. The solvent was then removed under reduced pressure, water (500 ml) and toluene (300 ml) were added followed by pH adjustment to 1-2 using concentrated hydrochloric acid. After separating the organic layer, ethyl acetate (500 ml) was added to the aqueous layer and pH was adjusted to 9-11 with liquid ammonia. The organic layer was separated and concentrated under reduced pressure to obtain oil. To this oily mass, acetone (750 ml) and activated charcoal (5 g) were added and stirred for 30 minutes. The reaction mixture was then filtered first through hyflo bed and then through micron filter. (L)-(+)-Tartaric acid was added to the filtrate and the reaction mixture was stirred for 4-5 hours and filtered. The solid thus obtained was washed with acetone and dried to obtain the title compound as solid

Example 8

Purification of (S)-(−)-Rivastigmine Tartrate 100 g of (S)-Rivastigmine tartrate was taken in methanol (200 ml) and heated to 45-50° C. to obtain a clear solution. The resulting hot reaction mass was filtered through micron filter and the filtrate was allowed to cool to −5 to 0° C. under stirring for 4-5 hours. The solid thus obtained was filtered, washed with chilled methanol and dried under reduced pressure at 45-50° C. for 12 hours to obtain the title compound.

Certain modification and improvements of the disclosed invention will occur to those skilled in the art without departing from the scope of invention, which is limited only by the appended claims.

We claim:

1. A process for producing (S)-3-[(1-dimethylamino)ethyl] phenyl-N-ethyl-N-methyl-carbamate (rivastigmine) of Formula I or its pharmaceutically acceptable salts, the process comprising:

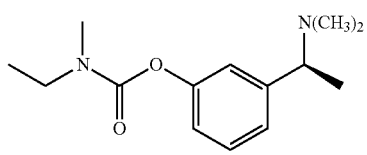

Formula I a) reacting a compound of Formula III with a protecting agent of Formula RX in presence of a base and solvent to obtain compound of Formula IV, Formula III Formula IV wherein R is selected from a substituted sulphonyl group and X is a halogen;

b) optically resolving the compound of Formula IV employing a resolving agent of compound HA to obtain a compound of Formula V;

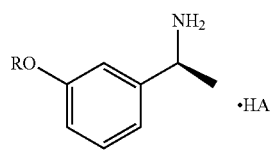

Formula V c) converting the diastereomeric compound of Formula V in presence of a base and a solvent to obtain a compound of Formula VI;

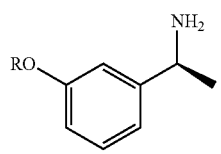

Formula VI d) methylating a compound of the Formula VI using a formylating agent in presence of an organic solvent to obtain a compound of Formula VII;

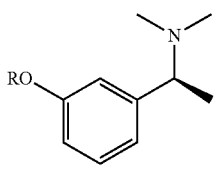

Formula VII e) deprotecting a compound of the Formula VII in presence of an acid or base to obtain a compound of Formula VIII;

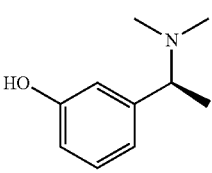

Formula VIII f) reacting a compound of Formula VIII with carbamoyl halide in presence of a base in a solvent to obtain rivastigmine of Formula I and further treating the resultant rivastigmine with an optically active acid to obtain a salt thereof.

2. The process according to claim 1, wherein the substituted sulphonyl group is selected from phenyl sulphonyl, $C_{1-4}$ alkyl substituted phenyl sulphonyl, $C_{1-4}$ alkoxy substituted phenyl sulphonyl, benzoyl sulphonyl or substituted benzoyl sulphonyl or any phenol protecting group.

3. The process according to claim 1, wherein the base used in step 1(a) is selected from an inorganic and an organic base.

4. The process according to claim 3, wherein the inorganic base is selected from alkali metal or alkaline earth metal hydroxide, carbonates, hydrides or mixture thereof.

5. The process according to claim 3, wherein the organic base is selected from the group comprising N,N-dimethylamine, N-ethyl-N-methyl amine, triethylamine, N,N-dimethylbenzylamine, N,N-diethylbenzylamine, N-methyl morpholine, dimethylaminopyridine, pyridine or mixture thereof.

6. The process according to claim 1, wherein the solvent used in step 1(a) is selected from aromatic hydrocarbon, straight or branched chain alcohols, chlorinated hydrocarbons, ketones, esters, ethers or mixture thereof.

7. The process according to claim 1, wherein the resolving agent is an optically active acid selected from mandelic acid, tartaric acid, camphor sulfonic acid, dibenzoyltartaric acid, or di-p-tolyl tartaric acid.

8. The process according to claim 1, wherein the resolution is carried out in a solvent selected from water, alcohol, ketones, ethers, esters or mixture thereof.

9. The process according to claim 1, wherein the base used in step 1(c) is selected from an inorganic or organic base.

10. The process according to claim 9, wherein the inorganic base is selected from ammonia or alkali metal or alkaline earth metal hydroxide, carbonates, hydride or mixture thereof.

11. The process according to claim 9, wherein the organic base is selected from N,N-dimethylamine, N-ethyl-N-methyl amine, triethylamine, N,N-dimethylbenzylamine, N,N-diethylbenzylamine, N-methyl morpholine or mixture thereof.

12. The process according to claim 1, wherein the solvent used in step 1(c) is selected from water, aromatic hydrocarbon, chlorinated hydrocarbons, esters, ethers or mixture thereof.

13. The process according to claim 1, wherein the formylating agent is selected from formic acid and formaldehyde solution or formaldehyde and sodium cyanoborohydride.

14. The process according to claim 1, wherein the organic solvent used in step 1(d) is selected from aromatic hydrocarbon, chlorinated hydrocarbons, esters, ethers, alcohol, nitriles, amides or mixture thereof.

15. The process according to claim 1, wherein the acid used during deprotection is an inorganic acid selected from hydrochloric acid, nitric acid, sulfuric acid, trifluoroacetic acid or mixture thereof.

16. The process according to claim 1, wherein the base used during deprotection is an inorganic base selected from alkali or alkaline earth metal hydroxide, carbonates, hydrides or mixture thereof.

17. The process according to claim 1, wherein the step of deprotection of the compound of Formula VII is carried out in presence of solvent selected from aromatic hydrocarbon, alcohols, ketones, esters, cyclic ethers, amides or mixture thereof.

18. The process according to claim 1, wherein the base used in step 1(f) is selected from an inorganic or organic base.

19. The process according to claim 1, wherein the solvent used in step 1(f) is selected from aromatic hydrocarbon, chlorinated hydrocarbons, esters, ethers, ketones, nitriles, amides or mixture thereof.

20. The process according to claim 1, wherein the optically active acid is selected from tartaric acid.

* * * * *

UNITED STATES PATENT AND TRADEMARK OFFICE
CERTIFICATE OF CORRECTION

PATENT NO. : 8,420,846 B2  Page 1 of 1
APPLICATION NO. : 13/060666
DATED : April 16, 2013
INVENTOR(S) : Dubey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 197 days.

Signed and Sealed this

Eighth Day of September, 2015

Michelle K. Lee
*Director of the United States Patent and Trademark Office*